(12) United States Patent
Sefton

(10) Patent No.: US 9,096,847 B1
(45) Date of Patent: Aug. 4, 2015

(54) METHODS FOR CONTROL, MEASUREMENT AND ENHANCEMENT OF TARGET MOLECULE PRODUCTION IN BIOELECTRIC REACTORS

(75) Inventor: Brian Sefton, Cupertino, CA (US)

(73) Assignee: Oakbio, Inc., Sunnyvale, CA (US)

( * ) Notice: Subject to any disclaimer, the term of this patent is extended or adjusted under 35 U.S.C. 154(b) by 859 days.

(21) Appl. No.: 13/034,596

(22) Filed: Feb. 24, 2011

Related U.S. Application Data

(60) Provisional application No. 61/308,050, filed on Feb. 25, 2010, provisional application No. 61/371,623, filed on Aug. 6, 2010.

(51) Int. Cl.
*C12N 13/00* (2006.01)
*C12P 1/00* (2006.01)
*C12P 7/00* (2006.01)

(52) U.S. Cl.
CPC .. *C12N 13/00* (2013.01); *C12P 7/00* (2013.01)

(58) Field of Classification Search
CPC .......... H01M 8/16; C02F 3/005; C12N 13/00; C12P 7/00
USPC ................................. 429/2; 435/41
See application file for complete search history.

(56) References Cited

U.S. PATENT DOCUMENTS

| | | | |
|---|---|---|---|
| 5,230,803 | A | 7/1993 | Thuer et al. |
| 5,686,276 | A | 11/1997 | Laffend et al. |
| 7,250,288 | B2 | 7/2007 | Zeikus et al. |
| 8,349,587 | B2 | 1/2013 | Fischer et al. |
| 8,518,566 | B2 | 8/2013 | Sefton |
| 2005/0247553 | A1 | 11/2005 | Ichikawa et al. |
| 2006/0051848 | A1 | 3/2006 | Nishio et al. |
| 2007/0099062 | A1 | 5/2007 | Leonida |
| 2007/0259216 | A1 | 11/2007 | Logan |
| 2007/0259217 | A1 | 11/2007 | Logan |
| 2008/0277273 | A1* | 11/2008 | Logan ........................... 204/253 |
| 2008/0292912 | A1 | 11/2008 | Logan et al. |
| 2009/0317882 | A1* | 12/2009 | Cheng et al. ................... 435/167 |
| 2010/0120104 | A1 | 5/2010 | Reed |
| 2010/0200495 | A1 | 8/2010 | Borole et al. |
| 2010/0227203 | A1 | 9/2010 | Ter Heijne et al. |
| 2011/0165667 | A1* | 7/2011 | Mets ........................... 435/297.1 |
| 2012/0288898 | A1* | 11/2012 | Lovley et al. .................... 435/92 |
| 2013/0078690 | A1 | 3/2013 | Reed |
| 2013/0089899 | A1 | 4/2013 | Kurek |

FOREIGN PATENT DOCUMENTS

| | | | |
|---|---|---|---|
| WO | 2007073598 | A1 | 7/2007 |
| WO | WO2007073598 | * | 7/2007 ............. H01M 8/16 |
| WO | 2009111513 | A1 | 9/2009 |
| WO | 2011088425 | A2 | 7/2011 |
| WO | 2012116338 | A1 | 8/2012 |

OTHER PUBLICATIONS

Pulse and Alternating Currents http://www.ee.sc.edu/personal/faculty/simin/ELCT102/15%20Pulse%20 &%20AC%20Circuits,%20Capacitors.pdf downloaded online Apr. 3, 2014.*
Watkinson, et al., Metallurgical Transactions B 13B: 369-378 (1982).
Goh, Ee-Been, et al., "Engineering of Bacterial Methyl Ketone Synthesis for Biofuels," Appl. Environ. Microbiol. 2012, 78(1):70, Oct. 28, 2011.
U.S. Appl. No. 12/726,980 non-final Office action, mailed Jan. 16, 2013.
U.S. Appl. No. 12/726,980 Applicant's Amendment B, submitted Apr. 16, 2013.
U.S. Appl. No. 12/875,708 non-final Office action, mailed Dec. 4, 2012.
U.S. Appl. No. 13/204,649 non-final Office action, mailed Aug. 27, 2013.
U.S. Appl. No. 13/204,649 Applicant's Amendment B, submitted Dec. 18, 2013.
U.S. Appl. No. 13/204,649 final Office action, mailed Mar. 26, 2014.
U.S. Appl. No. 13/204,649 Applicant's Amendment C, submitted May 20, 2014.
U.S. Appl. No. 13/204,649 Advisory Action, mailed Jun. 4, 2014.
U.S. Appl. No. 13/204,649 Applicant's Amendment D, submitted Jun. 26, 2014.
U.S. Appl. No. 13/610,844 non-final office action, mailed Feb. 11, 2014.
U.S. Appl. No. 13/610,844 Applicant's Amendment B, submitted May 12, 2014.
PCT/US12/54822 International Search Report and Written Opinion, mailed Jan. 16, 2013.
PCT/US10/27850 International Search Report and Written Opinion, mailed Jul. 28, 2010.
U.S. Appl. No. 13/610,844, filed Sep. 11, 2012, Brian Sefton, Chemoautotrophic Conversion of Carbon Oxides in Industrial Waste to Biomass and Chemical Products.
U.S. Appl. No. 13/204,649, filed Aug. 6, 2011, Brian Sefton, Chemoautotrophic Bioreactor Systems and Methods of Use.
U.S. Appl. No. 13/968,723, filed Aug. 16, 2013, Brian Sefton, Multi-Electrode Microbial Fuel Cells and Fuel Cell Systems and Bioreactors with Dynamically Configurable Flu.
U.S. Appl. No. 13/841,704, filed Mar. 15, 2013, Brian Sefton, Chemoautotrophic Methods and Microbes for Carotenoid Synthesis.

* cited by examiner

*Primary Examiner* — Taeyoon Kim
*Assistant Examiner* — Tiffany Gough
(74) *Attorney, Agent, or Firm* — Peters Verny, LLP

(57) ABSTRACT

Bioreactors comprising an electrical stimulation system supply a pulsed and/or modulated electrical input to microbes that use the electrical stimulation and available $CO_2$ to produce valuable organic compounds. Electrical power, such as from renewable sources remotely located with respect to the power grid, can be converted to chemical energy in the form of the organic compounds, which can be stored and/or transported readily.

11 Claims, 5 Drawing Sheets

METHODS FOR CONTROL, MEASUREMENT AND ENHANCEMENT OF TARGET MOLECULE PRODUCTION IN BIOELECTRIC REACTORS

CROSS-REFERENCE TO RELATED APPLICATIONS

This application claims the benefit of U.S. Provisional Patent Application No. 61/308,050 filed on Feb. 25, 2010 and entitled "Methods for Control, Measurement and Enhancement of Target Molecule Production in Bioelectric Reactors" and the benefit of U.S. Provisional Patent Application No. 61/371,623 filed on Aug. 6, 2010 and entitled "Bioelectric Synthesis Reactors and Methods of Use" both of which are incorporated herein by reference.

BACKGROUND OF THE INVENTION

1. Field of the Invention

The present invention relates generally to the field of bioelectrochemistry and more particularly to electrochemical synthesis bioreactors.

2. Description of the Prior Art

Living organisms transfer electrons through their electron transport chains as the core of their most basic metabolism. In aerobic organisms, oxygen is used as the final electron acceptor when it is combined with carbon to form carbon dioxide ($CO_2$). It has been shown that certain microbes are capable of depositing electrons onto other substances besides oxygen. The metal reducing bacteria are an example of this phenomenon in nature in that they utilize oxidized metals such as Fe(III) as a final electron acceptor. The ability of these and other microbes to directly deposit electrons onto electrodes, or onto intermediates which interact with the electrodes, is exploited in the Microbial Fuel Cell, (MFC). Among the many types of microbes capable of obtaining energy this way are those of genus *Geobacter* and *Shewanella*. It is also speculated that this phenomenon, referred to as 'exoelectrogenicity' is a characteristic of many species and does not have a strong corollary to phylogeny.

A less well understood natural phenomenon is the oxidation of inorganic compounds as a way for living organisms to derive energy. Such Chemoautotrophs obtain energy from the oxidation of inorganic compounds and obtain carbon from the fixation of carbon dioxide. Chemoautotrophic bacteria include nitrifying bacteria, sulfur-oxidizing bacteria, iron-oxidizing bacteria, and Knallgas-bacteria and Purple nonsulfur bacteria such as *rhodobacter capsulatus* which oxidize hydrogen. More recently it has been shown that some bacteria are able to either directly or indirectly derive energy via the uptake of electrons from electrodes supplying DC current. Microbes that fix carbon from $CO_2$ and obtain energy from electricity are known herein as electro-autotrophs. Energy can be obtained by some microbes by accepting an electron, while other microbes obtain energy by donating an electron.

In both the deposition and uptake of electrons, organisms rely on chemical carriers with specific oxidation or reduction potentials to pass the electrons from one to another while extracting energy to create new chemical bonds. In photosynthesis, for example, electrons from water, excited by light energy, are transferred through a variety of carriers and this energy is captured by being used to strip the carbon atom from $CO_2$ and bond it to another carbon. In heterotrophic organisms, electron transport is the method by which the energy contained in carbon-carbon bonds is harvested for use, as carbohydrates are broken during respiration. In the case of aerobic organisms, oxygen serves as the final electron acceptor when it is combined with carbon to form $CO_2$.

SUMMARY

The present invention provides methods of using microbes such as bacteria to synthesize organic compounds. Microbes in an aqueous solution in a bioreactor are provided with $CO_2$ and electricity, where the electricity is pulsed and/or modulated, to convert the electrical energy into chemical energy stored in the organic compounds produced by the microbes. By pulsing and modulating the electrical input, it is possible to more efficiently stimulate the resonant molecules of the microbes than is possible with continuous (non-pulsed) direct current stimulation, and to drive the microbial uptake, passing and release of electrons in an advantageous fashion An exemplary method of the invention comprises providing a vessel comprising electrodes disposed within an aqueous solution, where the aqueous solution includes a population of electro-autotrophic microbes. The method further comprises introducing carbon dioxide into the vessel, and applying a pulsed or modulated current between the electrodes, which in some embodiments is an alternating current (AC). In various embodiments providing the bioreactor includes providing a mediator in the aqueous solution. Also, in various embodiments, introducing carbon dioxide into the vessel comprises flowing air through the vessel, receiving waste gas from an industrial process, or receiving syngas or another gas mixture from a gasifier, torrefier, or any other system which uses pyrolysis. Introducing carbon dioxide into the vessel can also comprise receiving a gas mixture comprising carbon dioxide and/or hydrogen and/or methane. In place of introducing carbon dioxide into the vessel, carbon monoxide can instead be introduced, in some embodiments. Carbon monoxide can be introduced as part of a gas mixture including hydrogen and/or methane, for example.

In various embodiments the exemplary method further comprises measuring a system parameter of the bioreactor and using the measurement to control the pulsing or modulation of the applied current. System parameters can comprise, for example, temperature, pH, the concentration of the organic compound product, and the state of the microbes. Controlling the pulsing or modulation of the applied current can be useful to encourage the growth of one particular species or strain of microbe over another, to optimize the rate of production of the organic compound, to arrest, lengthen, or shorten microbial reproductive cycles, and to eliminate competitive species or strains.

In various embodiments the exemplary method further comprises recovering the organic compound, which can be performed within the vessel, in some embodiments. In other embodiments, the aqueous solution is transferred to a recovery system or unit which employs a separation technology to recover the organic compound. In still other embodiments the method further comprises performing a maintenance operation to deactivate, destroy or render inert all, or a particular, microbe within the vessel. In some instances, this is achieved by attenuating the electrical stimulation.

The present invention also provides bioreactors. An exemplary bioreactor of the invention comprises a vessel including an aqueous solution, where the aqueous solution contains a population of electro-autotrophic microbes such as electro-autotrophic bacteria or a consortium of bacteria including at least one that is electro-autotrophic. The electro-autotrophic microbes can produce an organic compound in response to the pulsed or modulated current, and in some embodiments the organic compound comprises octadecane. Optionally, the aqueous solution also comprises a mediator. The vessel also includes two or more electrodes disposed therein and contacting the aqueous solution. The bioreactor also comprises a controller in electrical communication between the two electrodes and configured to apply a pulsed or modulated current between the electrodes.

In various embodiments the vessel is divided into two chambers by a semi-permeable membrane, such as a proton exchange membrane, wherein one of the two electrodes is in each of the two chambers. The bioreactor optionally further comprises a sensor in electrical communication with the controller, such as a fluorescence detector, where measurements obtained from the sensor are used to control the electrical stimulation of the microbes.

The present invention also provides systems including one or more bioreactors. An exemplary system of the invention comprises a vessel including an aqueous solution containing a population of electro-autotrophic microbes, two electrodes disposed within the vessel and contacting the aqueous solution, and a controller in electrical communication between the two electrodes. The system also comprises a power supply such as a renewable energy source like a wind or solar farm. The controller is configured to receive power from the power supply and to apply a pulsed or modulated current between the electrodes. In various embodiments the system also comprises a recovery system designed to separate the organic compound from the aqueous solution.

DETAILED DESCRIPTION OF THE INVENTION

The present invention provides bioreactors comprising an electrical stimulation system capable of supplying a pulsed or modulated electrical input to supply electricity as the main source of energy for the microbes contained within the reactor, which may be genetically modified in some instances. The modulated electrical input can serve to increase growth rates, favor the growth of a particular species over others, and/or to select for the output of a desired product organic compound by preferentially driving an appropriate metabolic pathway.

An exemplary system comprises a vessel including an aqueous solution and at least two electrodes contacting the aqueous solution and connected externally via an electrical circuit including a controller. A particular electrode can be a dedicated anode or cathode, while in some embodiments an electrode may alternate between performing as an anode and a cathode, or may perform as an anode relative to some system components while simultaneously performing as a cathode relative to other system components.

Systems of the present invention find particular utility when paired with certain methods of electrical energy generation such as wind and solar. Because electricity is hard to store and transmit, the present invention allows electricity produced in remote locations, where such energy is abundant, to be converted to chemical energy in the form of an organic compound such as a dense and energy rich transportation fuel, for example. Thus, the systems of the present invention offer efficient conversion of electricity into liquid fuels which are easily stored and transported and which are compatible with existing fuel infrastructure and vehicles.

A further benefit of the systems of the present invention is that the carbon atoms that are incorporated into the product molecules are most commonly obtained by the removal of carbon from $CO_2$ molecules and the subsequent release of molecular oxygen ($O_2$). Thus, systems of the present invention can provide beneficial carbon capture. The $O_2$ by-product can be released harmlessly into the atmosphere or captured and sold, for example.

Exemplary product organic compounds that can be produced in this manner include naturally occurring and commercially synthesized molecules including fuel molecules and their precursors. It will be appreciated, therefore, that product organic compounds can include any molecule for which a metabolic pathway exists, or for which a suitable metabolic pathway can be genetically engineered into an organism. Product organic compounds include molecules that are traditionally synthesized from petroleum. As an example, octadecane, a commercially valuable hydrocarbon can be produced by the Knallgas-bacteria *Hydrogenothermus marinus*.

Figure 1:
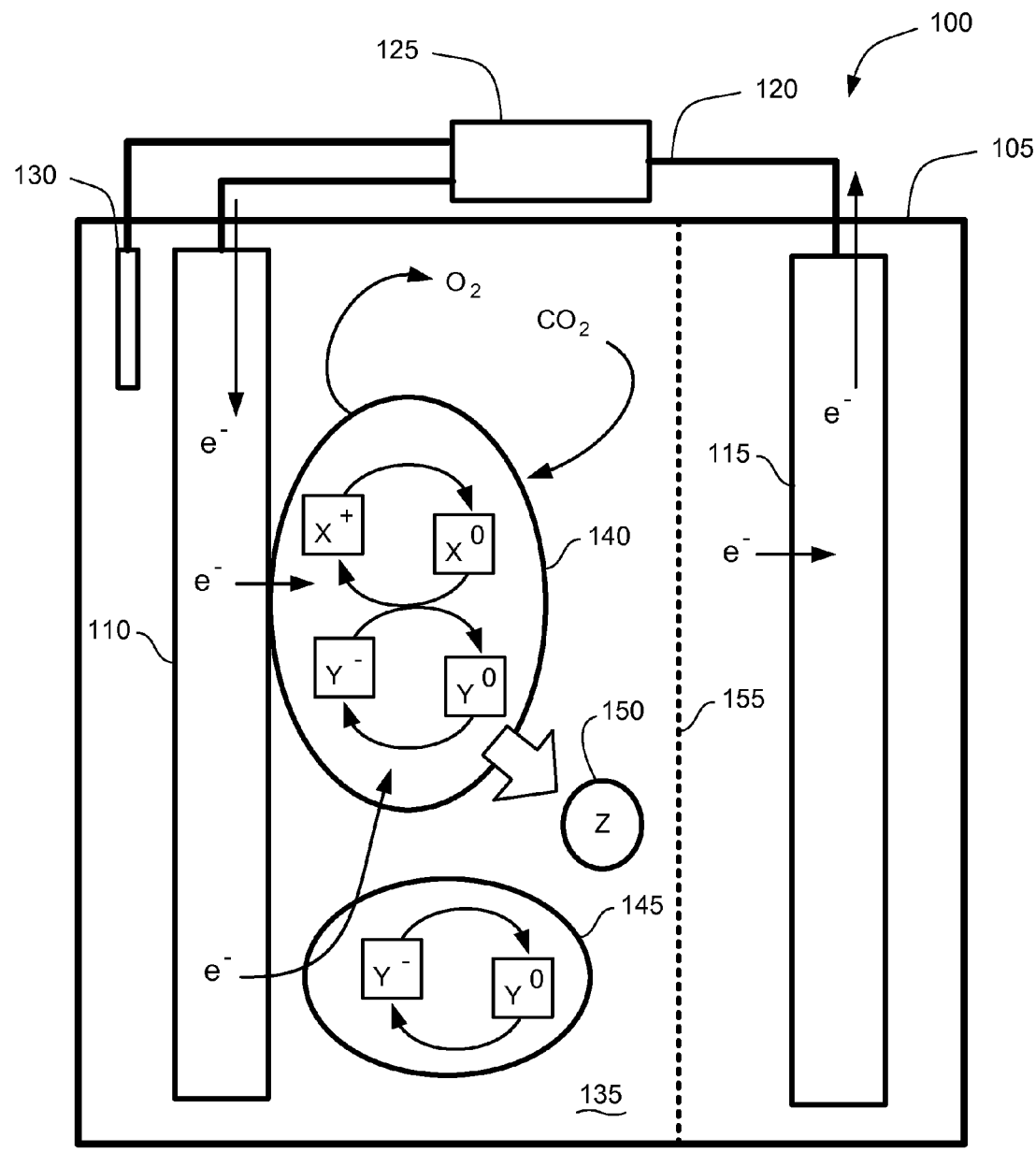
FIG. 1 is a schematic representation of a bioreactor according to an exemplary embodiment of the present invention.

FIG. 1 is a schematic representation of an exemplary bioreactor 100 of the present invention. The bioreactor 100 comprises a closed vessel 105 that is sealed from the surrounding environment except for various ports, discussed below, used to introduce and remove constituents from the interior of the vessel 105. The vessel 105 can comprise a tank made of a variety of materials including stainless steel. The bioreactor 100 further comprises at least two electrodes 110, 115, each disposed at least partially within the vessel 105, or disposed fully within the vessel 105 as illustrated. The electrodes are connected by way of an external electrical circuit 120 including a controller 125. The bioreactor 100 optionally also comprises a sensor 130 at least partially, or fully, disposed within the vessel 105 and in electrical communication with the controller 125. In some embodiments one or more of the electrodes 110, 115 can also serve as a sensor 130.

Various embodiments of the invention provide multiple electrodes 110 and 115. The electrodes 110, 115 can be arranged, for example, in parallel such that there is a first plurality of electrodes 110 arranged in parallel on one side of the external electrical circuit 120 and a second plurality of electrodes 115 arranged in parallel on the other side of the external electrical circuit 120. In further embodiments, electrodes 110, 115 in a plurality on either side of the external electrical circuit 120 may be controlled independently of the other electrodes in the plurality.

The bioreactor 100 further comprises an aqueous solution 135 including one or more types of microbes 140 which can comprise one or more species of bacteria, algae, fungi, and/or yeast. Optionally, the aqueous solution 135 may also include one or more mediators 145. The aqueous solution 135 may fill the entire vessel 105 else a headspace may be provided. In FIG. 1, the microbes 140 are represented by a single oval, but it will be appreciated that the oval is representative of an entire population of microbes 140 distributed throughout the aqueous solution 135, though not necessarily uniformly distributed. The aqueous solution 135 may additionally contain a mixture of chemicals which form a buffer system, or which comprise salts of various types. The aqueous solution 135 may additionally contain trace elements such as cobalt and nickel ions, as well as trace vitamins such as biotin.

Microbes 140 are characterized by metabolic pathways adapted to build organic compounds 150 by fixing carbon from $CO_2$ dissolved in the aqueous solution 135 using energy derived from electricity supplied by a power supply (not shown). Hydrolysis driven by the electricity may be used to dissociate water to provide the microbes with hydrogen necessary for generating hydrocarbon organic compounds.

The electrical power supply is coupled between the electrodes 110, 115 by the controller 125 which includes logic that is configured to bias the electrode 110 to be the cathode and electrode 115 to be the anode, or vice versa. Target organic compounds 150 produced by microbes 140 are represented generically by a circled 'Z' 150 in the aqueous solution 135 where the organic compounds 150 may be either soluble or insoluble therein. Exemplary bacteria include all genetically tractable microbes, from diverse genera including, but not limited to, *Escherichia, Rhodopseudamonas, Rhodobacter, Geobacter, Shewanella*, that produce organic compounds, perhaps using acetyl coenzyme A as a metabolic intermediate, and/or carbohydrates, to yield high value products such as alkanes, paraffins, kerosenes, phospholipids, lipopolysaccharides, fatty acids, and other biochemicals. In addition to the previously noted bacteria genera, microbes 140 can also comprise wild type, specific natural strains, or genetically modified strains of *Clostridium aceticum, Clostridium formicoaceticum, Geobacter lovleyi, Geobacter sulfurreducens, Heliobacterium modesticaldum, Hydrogenobacter thermophilus, Hydrogenovibrio marinus, Methanobacterium thermoautotrophicum, Methanococcus maripaludis, Methanosarcina acetivorans, Moorella thermoacetica* (nee *Clostridium thermoaceticum*), *Rhodopseudomonas palustris, Rhodopseudomonas viridis, Shewanella oniedensis, Sporomusa sphaeroides, Synechococcus elongatus, Rhodobacter capsulata, Rhodobacter spheroidies, Escherichia Coli*.

In various embodiments the microbes 140 can comprise a consortium of microbes of multiple species and/or of multiple strains of a species. A consortium may function in a variety of ways. For example, multiple microbial species may be involved in the production of a particular organic compound 150, where one species performs only part of the requisite steps to produce an intermediate product that a second species metabolizes to create the organic compound 150. It is also possible to have a synergistic consortium where some of the species perform tasks other than in the direct synthesis of the organic compound 150. Examples include maintaining conditions in the aqueous solution 135, such as scavenging oxygen, or removing or converting a by-product of another species. An exemplary consortium of bacteria is *Clostridium aceticum* and *Geobacter lovleyi*.

The aqueous solution 135 also can include one or more mediators 145, also represented in FIG. 1 by a single oval. A mediator 145 is a chemical which may be a single atom, such as iron, or a chemical compound, such as the pigment phenol red, capable of transferring electrons between an electrode 110, 115 and a microbe 140, or shuttle electrons from one chemical to another. A mediator 145 can act as either an oxidizer or a reducer depending on its reduction and/or oxidation state. Mediators 145 can be present in the aqueous solution 135 in several forms such as free-floating in the aqueous solution 135, attached, via a treatment, spontaneous or natural process, to the surfaces of the electrodes 110, 115, and/or attached to the microbes 140 or attached to other organisms within the aqueous solution 135. Mediators 145 may be generated via biological activity or exogenously added to the aqueous solution 135. Other examples of mediators 145 include metal cations, simple red, methyl blue, chemical compounds containing metal cations such as porphyrin structures, cytochromes, carotenoids, quinones, quinoliniums, polycyclic compounds, dyes, stains, and flurophores, or other chemicals capable of engaging in reduction-oxidation reactions.

In some cases molecular hydrogen ($H_2$) acts as a mediator 145. In these cases, molecular hydrogen is produced at an electrode 110 or 115 via hydrolysis of water, or from another compound, and serves as an electron donor to the microbes 140. Since the molecular hydrogen picks up an electron at an electrode 110 or 115 and transfers the electron to a microbe 140, the molecular hydrogen functions as a mediator 145. Other examples of mediators include compounds containing a metal ion in a positive oxidation state, or an organic cyclic compound, or poly-cyclic compound which serves as an electron shuttle between the electrode 110, 115 and the microbe 140.

Electrodes 110, 115 may comprise graphite, carbon, cement or polymer construction, or any material which is conductive. In FIG. 1 electrode 110 can be viewed as a cathode which provides electrons while electrical balance is maintained by electrode 115 which serves as an anode, or counter electrode, which accepts electrons. In various embodiments of the methods described below, the assignment of cathode and anode may repeatedly alternate between the electrodes 110, 115, under the control of controller 125. Electrical balance may also be maintained by a flow of protons from the anode to the cathode via the aqueous solution 135. Thus, a semi-permeable membrane 155 such as a proton exchange membrane is provided within the vessel 105, dividing the vessel into separate chambers. One or more sensors 130 can also be at least partially disposed within the aqueous solution 135 to allow properties of the system to be measured, as discussed further below.

The controller 125 serves to provide electrical stimulation to the microbes 140 in the aqueous solution 135 for the purpose of supplying energy to increase growth, favor particular species and increase, and/or select for, the output of desired product organic compounds. The controller 125 includes logic that is configured to receive electrical power from a power supply (not shown) and configured to use the power to apply a pulsed and/or modulated electrical stimulation to the microbes 140 via the electrodes 110, 115.

Pulsing can include the intermittent application of either DC or AC current between the electrodes 110, 115 such as in a square wave. In some embodiments, the polarity of each pulse can reverse such that the assignment of anode and cathode switches between electrodes 110 and 115 with each pulse. In other embodiments, polarity is maintained from one pulse to the next, and in still further embodiments more complex patterns of alternation between the two polarities are employed. The duration of time between pulses can be the same as the duration of the pulses themselves, shorter, longer, nonexistent, or can vary over time. In various embodiments the amplitude (e.g., the current) and/or duration of the pulses are the same over time, while in other embodiments either or both of the amplitude and duration vary over time. As an example, a train of pulses can begin with longer durations and low currents and over time transition to shorter durations and higher currents. Similarly, both the voltage applied between the electrodes 110, 115 and the electrical resistance of the external electrical circuit 120 can be held constant, or can vary in a pulsed manner. Pulsing can also comprise varied waveforms other than square waves, such as sawtooth waves and sinusoidal waves. In various embodiments the controller 125 includes logic that is configured to apply a pre-programmed regimen of pulses over time to the microbes 140. Pulsing is contrasted herein to, and excludes, continuous direct current.

Modulation, as used herein, refers to regulating, adjusting, or otherwise adapting the electrical stimulation according to either a pre-programmed regimen or dynamically responsive to measured conditions within the vessel 105 as determined by one or more sensors 130, or both. For example, the controller 125 can be configured to apply a duty cycle of 18 hours followed by a rest period of 6 hours during which no electrical stimulation occurs, and during the duty cycle pulses of current are applied at regular intervals but the voltage and current are regulated in response to measurements from a sensor 130. As one example, the sensor 130 can be configured to measure the concentration of the product organic compound 150 in the aqueous solution 135 and the controller 125 varies the current and/or voltage accordingly. To further this example, below a threshold concentration of the organic compound 150 the controller 125 applies a first regimen, then after the threshold is surpassed the controller 125 applies a second regimen. The controller 125 includes logic that can employ the output of a sensor 130 in a feedback loop to maintain conditions within the vessel 105, in some embodiments.

As noted, the bioreactor 100 can comprise a plurality of sensors 130. In various embodiments each electrode 110, 115 has a sensor 130 associated therewith in close proximity to the electrode 110, 115. Additionally, electrical properties of the external circuit 120 such as resistance can be monitored such that the electrodes 110, 115 serve as sensors 130. Additionally, any zone or location within the vessel 105 may contain one or more sensors 130. In some cases these sensors 130 consist of microbes that donate or receive electrons from an electrode, or a specially purposed electrode such as a reference electrode, or a section of an electrode 110, 115. Exemplary sensors 130 also include temperature sensors, pH sensors, pressure sensors, and organic carbon analyzers. Sensors 130 can also be provided to measure concentrations of inorganic and organic species in the aqueous solution 130.

In FIG. 1 the representative microbe 140 is illustrated as being in contact with the electrode 110 which is biased to be the cathode. This serves to illustrate that the concentration of the microbes 140 within the aqueous solution 135 may be non-uniform and in some instances may comprise a gradient that increases towards the cathode, whether electrode 110 or 115. At the cathode, the microbes 140 are able to receive electrons through direct contact or through the action of mediators 145. The gradient can dissipate if the polarity is switched, and may reform at the opposite electrode if the time between pulses is sufficiently long. Because of the population gradient, other gradients may also exist in the aqueous solution 135, and it will be understood that the location of sensors 130 within the vessel 105 should take this into account.

Figure 2:
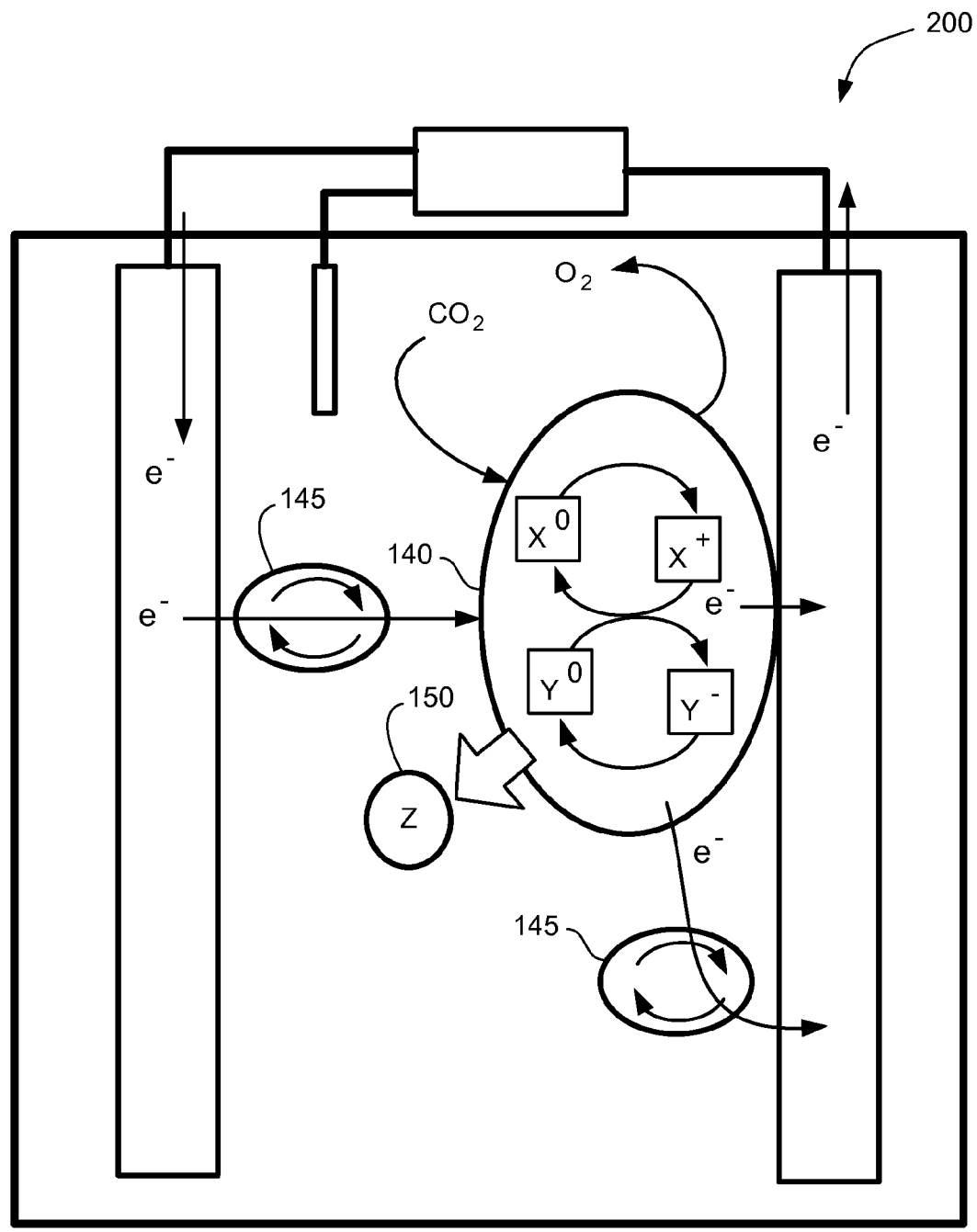
FIG. 2 is a schematic representation of a bioreactor according to another exemplary embodiment of the present invention.

FIG. 2 represents a bioreactor 200 that is structurally similar to the bioreactor 100 of FIG. 1. In bioreactor 200, however, the microbes 140 donate electrons at the anode, rather than accept electrons at the cathode. Examples of these microbes 140 are *Geobacter metallreductans* and *Shewanella Oneidensis*. Hybrid bioreactors can employ both types of microbes 140 such that some microbes 140 accept electrons at the cathode while simultaneously other microbes 140 donate electrons at the anode. Additionally, FIG. 2 illustrates that mediators can both transfer electrons to and from the microbes 140.

Figure 3:
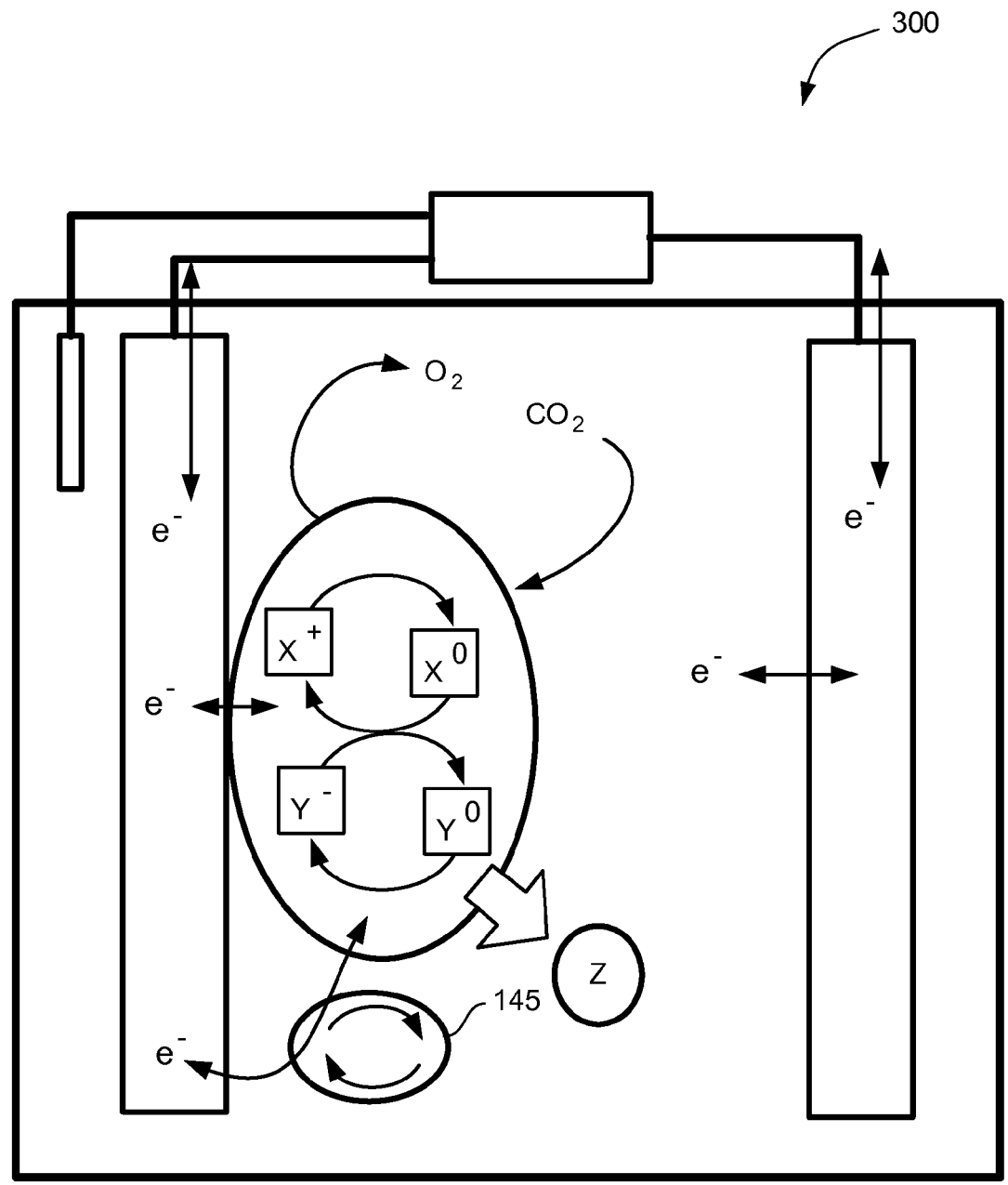
FIG. 3 is a schematic representation of a bioreactor according to still another exemplary embodiment of the present invention.

FIG. 3 represents a bioreactor 300 that is structurally similar to the bioreactor 100 of FIG. 1. In bioreactor 300, however, the controller 125 includes logic that is configured to apply alternating current between the electrodes 110, 115. Because the mobility of the microbes 140 in the aqueous solution 135 is very low over the time scales with which the polarity of the current alternates, microbes 140 are not drawn to one electrode 110, 115 or the other and can receive and deposit electrons onto the same electrode 110, 115 either directly or through mediators 145. In bioreactors 300, the frequency of the alternating current is a key variable, as are the waveform, current, and resistance of the external electrical circuit 120. Accordingly, it will be understood that AC, as used herein, is not limited to 60 Hz but can comprise a frequency tuned to a particular metabolic pathway of the microbes 140.

Figure 4:
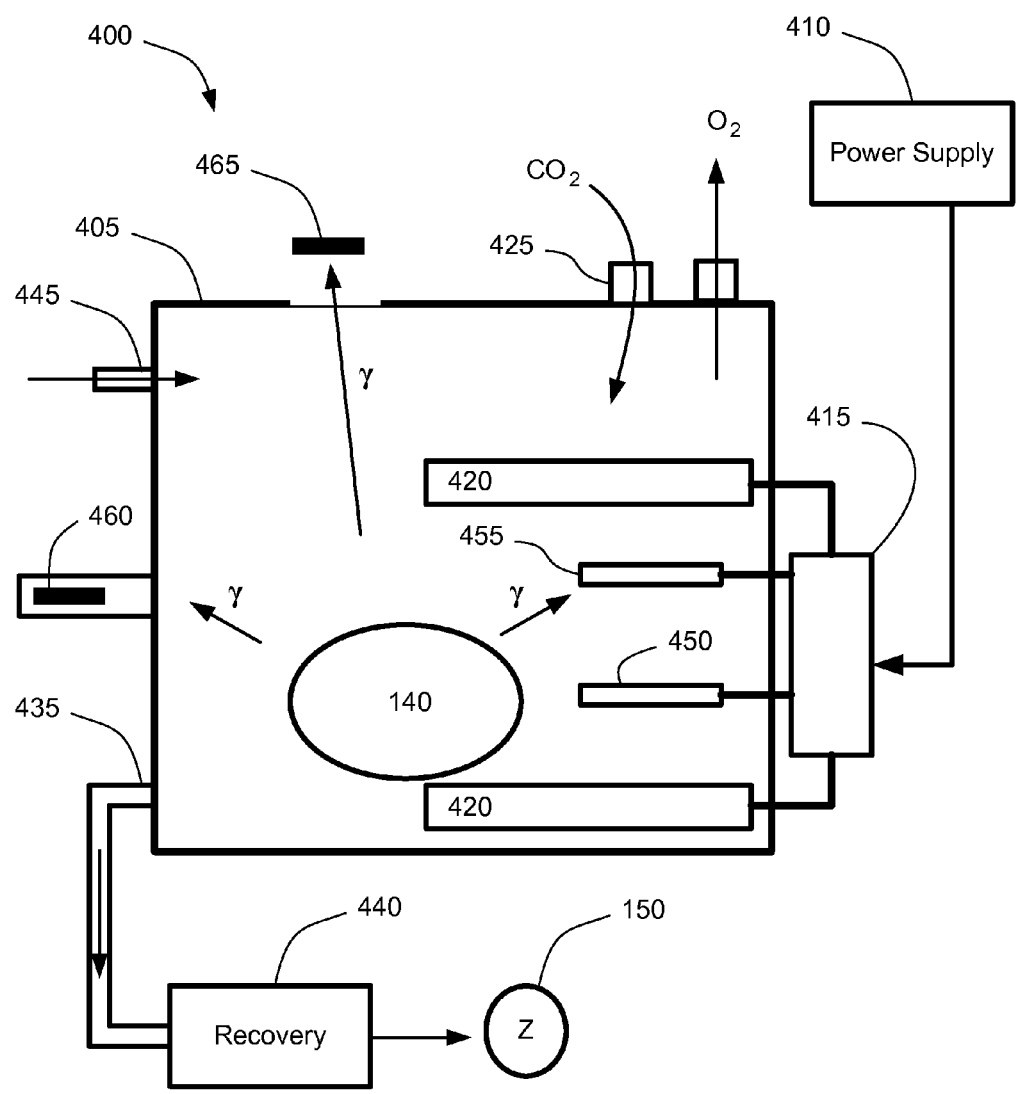
FIG. 4 is a schematic representation of a bioreactor according to yet another exemplary embodiment of the present invention.

FIG. 4 represents another exemplary system 400 of the present invention. Systems 400 can include, in some embodiments, a bioreactor 405 as generally described above with respect to bioreactors 100, 200, and 300, and a power supply 410 that can comprise an electrical energy generation system, such as a wind or solar farm. Power supply 410 can also comprise the electrical power grid, in some embodiments. Power from the power supply 410 is received by a controller 415 of the bioreactor 405 which applies a pulsed and/or modulated electrical stimulation to microbes 140 through electrodes 420 to convert electrical energy to chemical energy in the form of an organic compound 150.

The bioreactor 405 also includes several gas ports. A first gas port 425 allows $CO_2$ to enter the bioreactor 405 while a second gas port 430 permits evolved gases such as $O_2$ to be vented to the atmosphere or collected as a further product. In some embodiments, the system 400 includes a source of $CO_2$ (not shown), such as the flue gas from a power plant, or another source of $CO_2$-rich gas. In other embodiments, the bioreactor 405 obtains $CO_2$ by receiving air through the port 425. Although illustrated herein as a passive opening at the top of the bioreactor 405, it will be appreciated that embodiments of bioreactor 405 can include means for improving the dissolution of $CO_2$ into the aqueous solution 135 such as a gas manifold or sparger configured to bubble gas into the aqueous solution 135.

The bioreactor 405 also includes also a port 435 for withdrawing the organic compound 150. In some embodiments the organic compound 150 is not miscible in the aqueous solution 135 and can be withdrawn directly through the port 435, while in other embodiments aqueous solution 135 including the organic compound 150 is withdrawn through the port 435 and processed through a recovery system 440 that employs an separation technology that is appropriate to the organic compound 150. For example, octadecane can be removed from the aqueous solution 135 by reducing the temperature of the aqueous solution 135 below a threshold below which the octadecane forms a waxy substance that can be skimmed from the surface of the aqueous solution 135. Fluid withdrawn from the bioreactor 405 can be replaced through another fluid port 445. In some embodiments, the aqueous solution 135 recovered from the recovery system 440 is recycled back into the bioreactor 405 through the port 445.

The bioreactor 405 can also include one or more sensors such as reference electrode 450, and one or more of fluorescence detectors 455, 460, and 465. Fluorescence detectors can be used to observe the natural fluorescence that occurs when the electron transport chain and internal electron carriers of the microbes 140 are electrically stimulated. Fluorescence detector 455 is disposed in the aqueous solution 135 and is in electrical communication with the controller 415. Fluorescence detectors 460 and 465 are likewise in electrical communication with the controller 415, though the connections have been omitted for clarity. Fluorescence detector 460 lies outside of the vessel of the bioreactor 405, but is in fluid communication therewith. Fluorescence detector 465 also lies outside of the vessel of the bioreactor 405 and receives fluorescence through a window. As one example, fluorescence detectors 455, 460, or 465 can measure the fluorescence of cellular chemical components, such as cytochromes, in response to the electrical stimulation of the metabolic processes, where the measured intensity of the fluorescence can be correlated to the concentration of the microbes 140.

Other exemplary sensors of the bioreactor 405 are configured to measure gas consumption, gas emission, total organic carbon, chemical composition and/or presence, absence, rate of production or rate of consumption of any individual or combination of chemicals, ionic strength and composition, electrical properties, columbic balance, reduction and or oxidation potentials, fluorescence, optical properties, flow rate, pH, pressure, and temperature. Any of these parameters can be used by logic residing in the controller 415 to dynamically control electrical pulsing and/or modulation.

In further embodiments, the system 400 can comprise multiple bioreactors 405 each separately controllable but receiving power from the same power supply 410 and/or receiving $CO_2$ from the same $CO_2$ supply. Multiple bioreactors 405 can be connected together through controllable electrical and fluidic connections to generate larger integrated bioreactor systems 400. The fluidic connections can employ valves, junctions and other connections of various configurations. In some of these embodiments, the microbes 140 in different bioreactors 405 are different. For instance, one bioreactor 405 can include a microbe 140 that produces a first organic compound 150 that is converted by a different microbe 140 in the next bioreactor 405 to a second organic compound 150.

Figure 5:
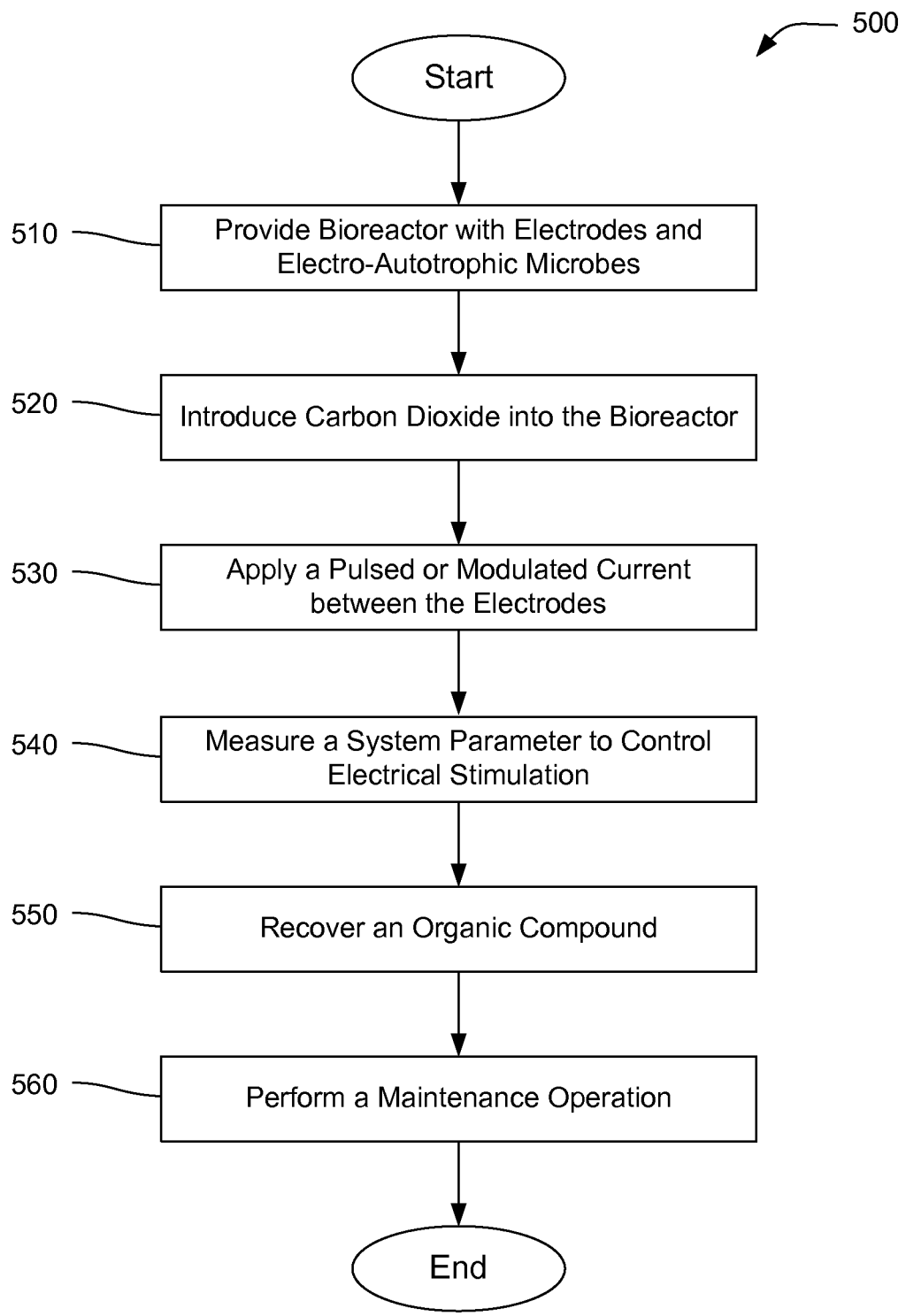
FIG. 5 is a flowchart representation of a method of producing an organic compound according to an exemplary embodiment of the present invention.

FIG. 5 is a flowchart representation of an exemplary method 500 of the present invention. The method 500 comprises a step 510 of providing a bioreactor and more specifically of providing a vessel comprising electrodes disposed within an aqueous solution, where the aqueous solution includes a population of electro-autotrophic microbes. In a step 520 $CO_2$ is introduced into the vessel, and in a step 530 a pulsed and/or modulated current is applied between the electrodes. Optionally, providing the bioreactor in step 510 includes also providing a mediator along with the population of electro-autotrophic microbes in the aqueous solution. In various embodiments introducing $CO_2$ into the vessel comprises receiving waste gas from an industrial process such as flue gas from a power plant, while in other embodiments introducing $CO_2$ into the vessel comprises flowing air through the vessel. Introducing $CO_2$ into the vessel may also comprise receiving syngas, or another gas output from a gasifier, torrefier, or any other system which uses pyrolysis. Introducing carbon dioxide into the vessel can also comprise receiving a gas mixture comprising carbon dioxide and/or carbon monoxide and/or hydrogen and/or methane, such as from a steam reformation or water-shift process. In any case, introducing $CO_2$ into the vessel can comprise bubbling the gas, whether a waste gas, air, or another $CO_2$-bearing gas, through the aqueous solution. In place of $CO_2$, in some embodiments carbon monoxide supplies the carbon. In such alternative embodiments a step of receiving CO replaces step 520. In these embodiments the carbon monoxide can be provided in a gas mixture including hydrogen and/or methane, for example.

In step 530 a pulsed or modulated current is applied between the electrodes, and in some embodiments the current is both pulsed and modulated. By employing an alternating current, in some embodiments, each electrode is both donor and acceptor of electrons depending on the phase of the cycle. Direct current can also be pulsed and/or modulated in step 530. Electron uptake rate and efficiency of the microbes, and the production of desired organic molecules, are optimized by pulsing and/or modulating the current applied between the electrodes. By modulating and pulsing current or power it is possible to more finely control the metabolism of microbes which derive their primary sustenance from the electrical input. Many of the metabolic processes and chemicals involved in metabolism are resonant. Supplying pulsed and/or modulated power can increase the absorption efficiency of electrons by the microbes, and can favor metabolic processes that preferentially produce a particular molecule over others. Furthermore, aspects of the applied electrical stimulation, such as the waveform, voltage, and other electrical parameters, can be modulated in response to measurements from sensors to further increase efficiency and selectivity. Applying pulsed and/or modulated power, combined with measurement allows for the control of the reproduction cycles of the microbes by controlling their relative energy levels, and other factors.

In an optional step 540 the conditions within the bioreactor are monitored and used to control the electrical stimulation of the microbes, i.e., the pulsing and/or modulation of the applied current. System parameters that can be measured include temperature, pressure, pH, the concentrations of species in the aqueous solution such as the concentration of an organic compound product, the population density of microbes in a region or zone within the vessel, and where the microbes are in their life cycle, referred to herein as the state of the microbes. System parameters can be measured with sensors and/or by monitoring the electrical response of the system to the applied stimulation. For example, rates and the electrical parameters of electron deposition by organisms in response to initiation and cessation of power are useful metrics for system control decisions. Pulsing and/or modulating current can also encourage the growth of one particular species or strain of microbe over another and therefore can be adjusted in response to measurements of the relative populations. Microbe reproduction cycles can be controlled to be shorter, longer, or arrested, in various embodiments. Additionally, specific microbial sub-populations or strains can be preferentially selected, and competitive species or strains can be eliminated.

In an optional step 550 the organic compound is recovered. The organic compound may be recovered from the vessel itself, or the aqueous solution including the organic compound can be transferred to a recovery system or unit that can separate the organic compound from the aqueous solution. Applicable separation technologies include but are not limited to, precipitation, distillation, column chromatography, filtering, centrifugation, absorption, adsorption, affinity, phase separation, flow based and many other methods.

In an optional step 560 a maintenance operation can be performed to deactivate, destroy or render inert all, or a particular, microbe within the vessel. In some embodiments this is achieved by attenuating the electrical stimulation.

Logic described herein can comprise, for example, hardware, such as application-specific integrated circuits (ASICs), specifically designed to perform the particular described functions. Logic can also comprise firmware residing, for instance, in read only memory (ROM) or flash memory, where the firmware is programmed to perform the particular described functions. Logic can also comprise a microprocessor capable of executing software residing in a memory, for example, in random access memory (RAM), where the computer instructions embodied in the software, when executed by the microprocessor perform the particular described functions. Any combination of two or more of hardware, firmware, and software can also comprise logic.

In the foregoing specification, the invention is described with reference to specific embodiments thereof, but those skilled in the art will recognize that the invention is not limited thereto. Various features and aspects of the above-described invention may be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

What is claimed is:

1. A method of creating an organic compound comprising:
providing a vessel comprising electrodes disposed within an aqueous solution including a population of electro-autotrophic microbes, the vessel further comprising a controller in electrical communication between the two electrodes and configured to receive power from a power supply and to apply a pulsed or modulated current between the electrodes;
introducing carbon dioxide into the vessel; and
applying a pulsed or modulated current between the electrodes, wherein the electro-autotrophic microbes fix carbon from the carbon dioxide introduced into the vessel to produce the organic compound in response to the pulsed or modulated current.

2. The method of claim 1 wherein providing the bioreactor includes providing a mediator in the aqueous solution.

3. The method of claim 1 wherein introducing carbon dioxide into the vessel comprises receiving waste gas from an industrial process.

4. The method of claim 1 wherein the applied current is an alternating current.

5. The method of claim 1 further comprising measuring a system parameter of the bioreactor and using the measurement to control the pulsing or modulation of the applied current.

6. The method of claim 5 wherein the system parameter comprises a concentration of the organic compound.

7. The method of claim 5 wherein the system parameter comprises a state of the microbes.

8. The method of claim 1 further comprising recovering the organic compound.

9. The method of claim 1 wherein introducing carbon dioxide into the vessel comprises receiving syngas.

10. The method of claim 1 wherein introducing carbon dioxide into the vessel comprises receiving a gas mixture comprising carbon dioxide and either hydrogen or methane.

11. The method of claim 8 wherein the recovered organic compound is other than the population of electro-autotrophic microbes.

* * * * *